United States Patent
Feng et al.

(10) Patent No.: US 11,630,173 B2
(45) Date of Patent: Apr. 18, 2023

(54) RADIO FREQUENCY COIL UNIT WITH PRESSURE RESERVOIR FOR MAGNETIC RESONANCE IMAGING

(71) Applicant: GE Precision Healthcare LLC, Milwaukee, WI (US)

(72) Inventors: Limin Feng, Solon, OH (US); Pei Hsuon Chan, Aurora, OH (US); Aleksey Zemskov, Solon, OH (US); Jason Lee Philps, Hartland, WI (US); Kristen Frederick, Parma, OH (US); Ghazi Mustafa, North Royalton, OH (US); Michael Oveson, Salt Lake City, UT (US)

(73) Assignees: GE PRECISION HEALTHCARE LLC, Milwaukee, WI (US); INTERMOUNTAIN INTELLECTUAL ASSET MANAGEMENT, LLC, Salt Lake City, UT (US)

( * ) Notice: Subject to any disclaimer, the term of this patent is extended or adjusted under 35 U.S.C. 154(b) by 711 days.

(21) Appl. No.: 16/546,228

(22) Filed: Aug. 20, 2019

(65) Prior Publication Data
US 2021/0055362 A1   Feb. 25, 2021

(51) Int. Cl.
*G01R 33/34* (2006.01)
*G01R 33/3415* (2006.01)
(Continued)

(52) U.S. Cl.
CPC ........ *G01R 33/34084* (2013.01); *A61B 5/055* (2013.01); *A61B 5/6843* (2013.01); *G01R 33/3415* (2013.01); *A61B 2503/04* (2013.01)

(58) Field of Classification Search
None
See application file for complete search history.

(56) References Cited

U.S. PATENT DOCUMENTS

| 8,469,911 | B2 | 6/2013 | Hiebert |
| 2010/0137704 | A1* | 6/2010 | Vij .......................... A61B 5/055 606/1 |

(Continued)

FOREIGN PATENT DOCUMENTS

| WO | 2018098248 A1 | 5/2018 |
| WO | WO 2018098331 | * 5/2018 |

OTHER PUBLICATIONS

Fuqua, H. et al., "Systems for a Radio Frequency Coil for MR Imaging," U.S. Appl. No. 62/426,010, filed Nov. 23, 2016, 49 pages.

(Continued)

*Primary Examiner* — Shahdeep Mohammed
(74) *Attorney, Agent, or Firm* — McCoy Russell LLP

(57) ABSTRACT

Various methods and systems are provided for radio frequency coil units for magnetic resonance imaging. In one example, a radio frequency (RF) coil unit for magnetic resonance imaging (MM) includes an outer layer forming an exterior of the RF coil unit, a pressure reservoir enclosed by the outer layer, wherein the pressure reservoir forms a sealed chamber, and an array of RF coil elements enclosed by the outer layer, wherein the array of RF coil elements is disposed outside of the sealed chamber of the pressure reservoir.

20 Claims, 7 Drawing Sheets

(51) Int. Cl.
   *A61B 5/00*     (2006.01)
   *A61B 5/055*    (2006.01)

(56) References Cited

U.S. PATENT DOCUMENTS

| | | |
|---|---|---|
| 2013/0317346 A1 | 11/2013 | Alagappan et al. |
| 2014/0021949 A1* | 1/2014 | Heismann .............. G01R 33/34 |
| | | 324/322 |
| 2017/0062971 A1 | 3/2017 | Boyland et al. |
| 2017/0095365 A1* | 4/2017 | Reese ................. G01R 33/3415 |
| 2019/0310329 A1* | 10/2019 | Malik .................... A61B 5/055 |

OTHER PUBLICATIONS

Stack, C. et al., "RF Coil Array for an MRI System," U.S. Appl. No. 62/590,248, filed Nov. 22, 2017, 84 pages.

* cited by examiner

RADIO FREQUENCY COIL UNIT WITH PRESSURE RESERVOIR FOR MAGNETIC RESONANCE IMAGING

FIELD

Embodiments of the subject matter disclosed herein relate to radio frequency (RF) coil for magnetic resonance imaging (MRI), and more particularly, to surface coils with pressure reservoir for MRI.

BACKGROUND

Magnetic resonance imaging (MRI) is a medical imaging modality that can create images of the inside of a human body without using x-rays or other ionizing radiation. MRI systems include a superconducting magnet to create a strong, uniform, static magnetic field $B_0$. When an imaging subject is placed in the magnetic field $B_0$, the nuclear spins associated with the hydrogen nuclei in the imaging subject become polarized such that the magnetic moments associated with these spins become preferentially aligned along the direction of the magnetic field $B_0$, resulting in a small net magnetization along that axis. The hydrogen nuclei are excited by a radio frequency signal at or near the resonance frequency of the hydrogen nuclei, which add energy to the nuclear spin system. As the nuclear spins relax back to their rest energy state, they release the absorbed energy in the form of a radio frequency (RF) signal. This RF signal (or MR signal) is detected by one or more RF coil units and is transformed into the image using reconstruction algorithms.

In order to detect the RF signals emitted by the body of the subject, an RF coil unit is often positioned proximate anatomical features to be imaged by the MM system. Quality of images produced by the MRI system is greatly influenced by how closely the RF coil unit conforms to the contours of the body of the subject during the image acquisition.

BRIEF DESCRIPTION

In one embodiment, a radio frequency (RF) coil unit for magnetic resonance imaging (MM) includes an outer layer forming an exterior of the RF coil unit, a pressure reservoir enclosed by the outer layer, wherein the pressure reservoir forms a sealed chamber, and an array of RF coil elements enclosed by the outer layer, wherein the array of RF coil elements is disposed outside of the sealed chamber of the pressure reservoir.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

Figure 1:
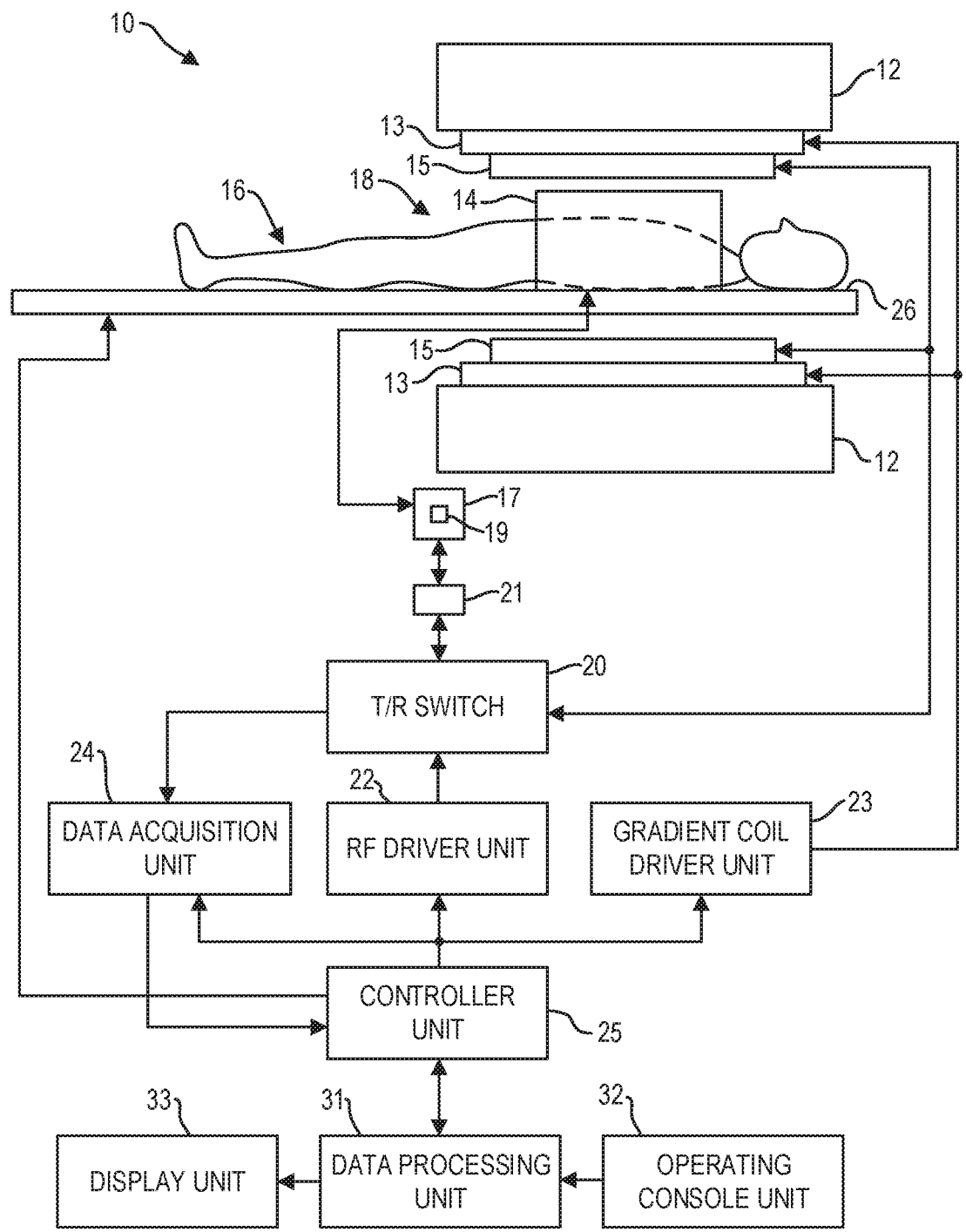
FIG. 1 is a block diagram of an Mill system, according to an exemplary embodiment.

The drawings illustrate specific aspects of the described an RF coil unit with a pressure reservoir for MM. Together with the following description, the drawings demonstrate and explain the principles of the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

Figure 3:
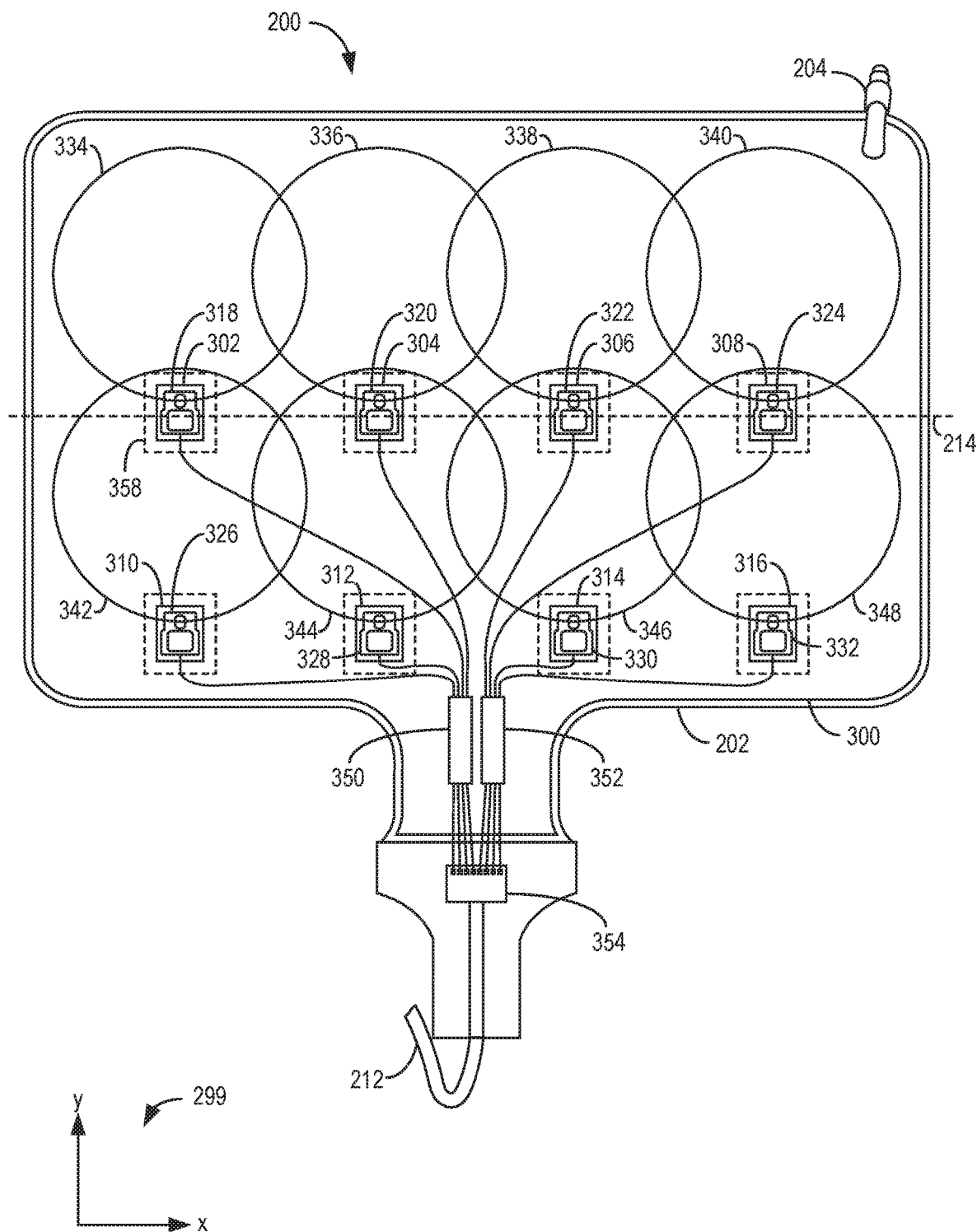
FIG. 3 shows an interior portion of the RF coil unit of FIG. 2, according to an exemplary embodiment.
Figure 4:
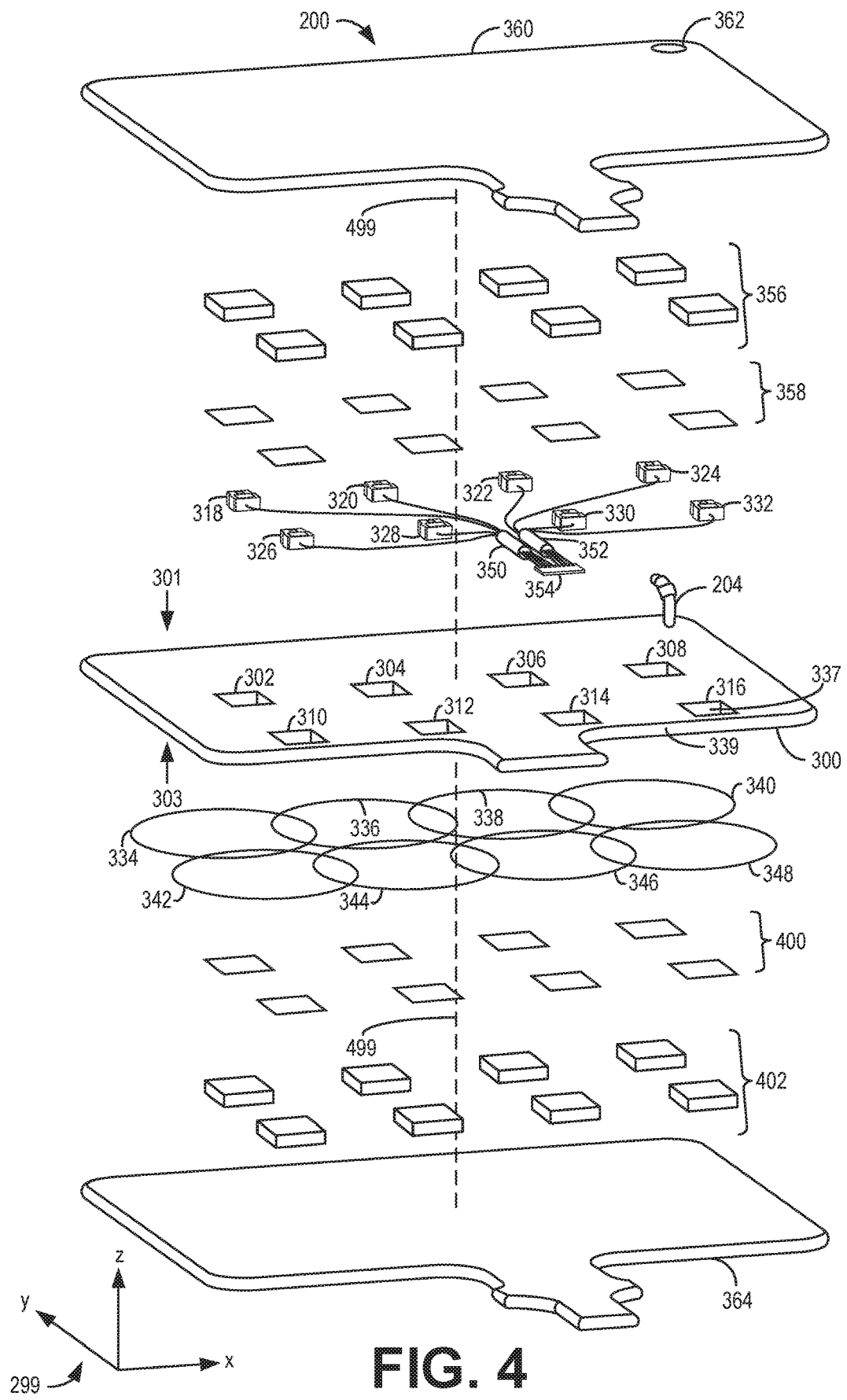
FIG. 4 shows an exploded view of the RF coil unit of FIGS. 2-3, according to an exemplary embodiment.
Figure 5:
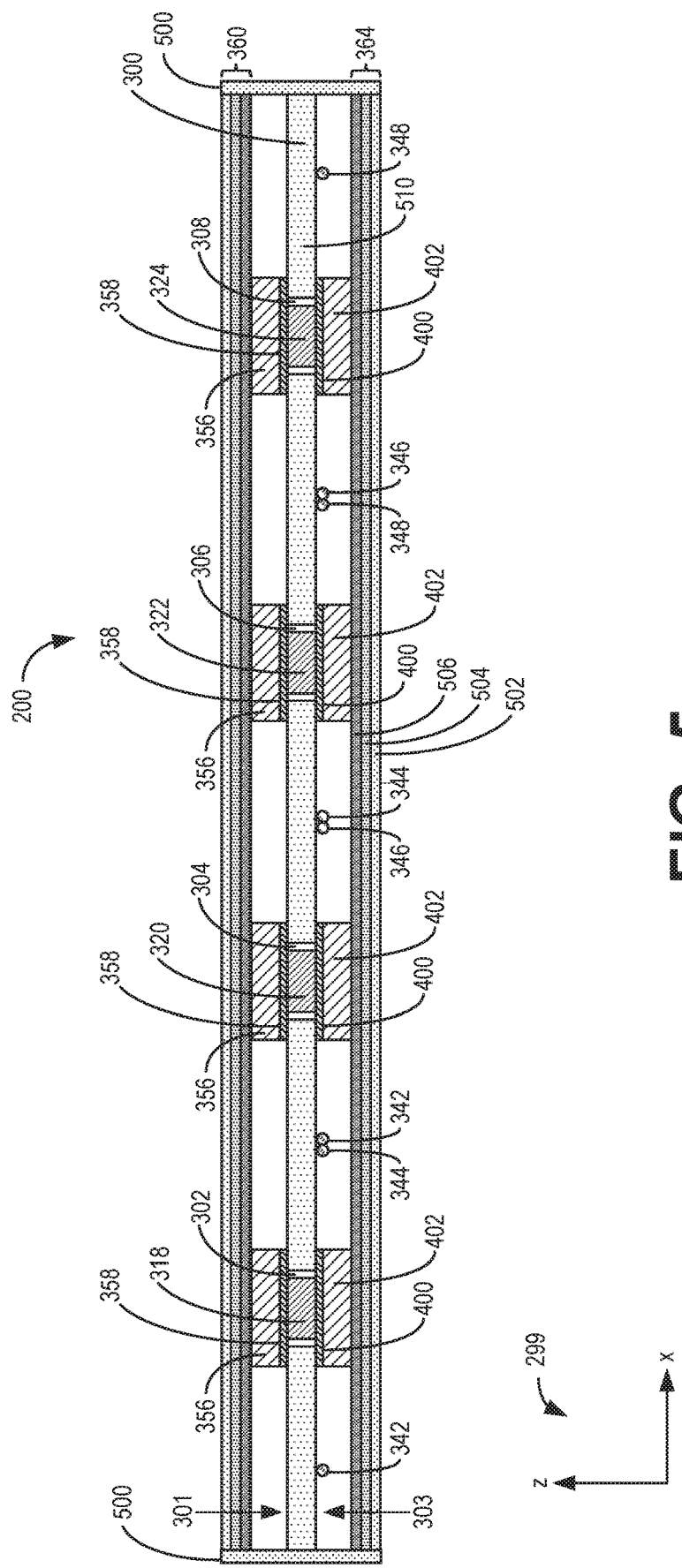
FIG. 5 shows a cross-sectional view of the RF coil unit of FIGS. 2-4, according to an exemplary embodiment.

The following description relates to various embodiments for an RF coil unit. A magnetic resonance imaging (MM) system, such as the MRI system shown by FIG. 1, may include an RF coil unit, such as the RF coil unit shown by FIG. 2. The RF coil unit includes a plurality of flexible RF coil elements (which may be referred to herein as RF coils) and an adjustable pressure reservoir. The pressure reservoir is positioned within an interior formed by an outer layer of the RF coil unit and includes a plurality of openings shaped to receive coupling electronics of the flexible RF coil elements, as shown by FIG. 3. An interior of the pressure reservoir is a sealed chamber that is fluidly isolated from the interior of the RF coil unit as shown by FIG. 4, and a pressure within the interior of the pressure reservoir is adjustable via a fluid passage arranged to extend through the outer layer of the RF coil unit. The coupling electronics seat within the openings of the pressure reservoir, as shown by FIG. 5. A pressure within the pressure reservoir may be adjusted via the fluid passage, in order to form the RF coil unit to a body of a subject to be imaged by the MRI system, as shown by FIGS. 6-13. A loop portion of each RF coil element, as shown by FIG. 14, may bend or flex with the pressure reservoir as the RF coil unit is formed to the body of the patient. As such, the loop portion of each RF coil element may be positioned closer to the body of the patient as the RF coil unit is formed to the body, and an imaging signal-to-noise ratio (SNR) of the RF coil unit may be increased.

The RF coil unit may be used to image a variety of different anatomical structures of a subject (e.g., a foot, shoulder, Cervical-spine, etc. of the subject) without the use of straps or other fixtures. Imaging anatomical structures via conventional RF coil units may be more difficult due to variance in the shape and size of the anatomical structures for different subjects (e.g., patients). However, by configuring the RF coil unit as described herein, the RF coil unit may be adapted to image a large variety of anatomical structures for patients of different shape and/or size. The pressure reservoir may maintain its shape while formed to the body by adjusting the pressure within the interior of the pressure reservoir. The flexibility of the RF coil elements maintains the RF coil elements close to the anatomy to be imaged. Further, because the RF coil unit may form to the body without the use of straps or other fasteners, cost of the RF coil unit may be reduced relative to conventional RF coil units that couple via straps or other fasteners and fixtures, and time to setup the RF coil unit for imaging may be reduced.

In some embodiments, the RF coil unit may be used as a stabilizer for pediatric scans by adjusting the pressure within the pressure reservoir to form the RF coil unit to the body. Motion of the subject during a scan (e.g., during imaging via the MRI system) may result in imaging artifacts. Improved rigidity of the RF coil unit during the scan may reduce imaging artifacts by reducing the likelihood of movement of the subject. As one example, adjusting the pressure (e.g., gas pressure) within the pressure reservoir may increase the rigidity of the RF coil unit by compressing plastic pellets (e.g., polystyrene pellets) disposed within the pressure reservoir. The increased rigidity of the RF coil unit may sufficiently reduce movement of the subject to be imaged during a pediatric scan (e.g., imaging of an infant). Because the pressure reservoir is positioned within the RF coil unit, the RF coil unit may maintain the position of the subject to be imaged without additional straps and/or other fasteners. Additionally, the outer layers of the RF coil unit may be formed of a soft, fabric material in order to increase patient comfort.

In this configuration, the RF coil unit is positioned against the body of the subject such that the RF coil elements are arranged between the body and the pressure reservoir. This arrangement may increase patient comfort and positions the RF coils elements close to the body. As a result, the SNR of images of the subject obtained by the MRI system via the RF coil unit may be increased.

In some embodiments, the RF coil unit may include eight (8) RF coil elements. The RF coil elements may be arranged along a layer of flexible cloth material, such as a fabric, with the pressure reservoir positioned against the loop portion of each RF coil element (e.g., such that the loop portions are positioned between the layer of cloth and the pressure reservoir). The RF coil elements each include a loop portion and a coupling electronics portion. The loop portion of each RF coil element may be fixed (e.g., stitched) to the cloth material. In other embodiments, the cloth material may be positioned between the loop portions and the pressure reservoir, with the loop portions fixed to the cloth material. The coupling electronics of the RF coil elements (e.g., feed boards) are placed through the openings extending through a thickness of the pressure reservoir to enable cables (e.g., electrical wires) coupled to the RF coil elements to be positioned at an opposing side of the pressure reservoir (e.g., a side opposite to the side at which the loop portions are positioned). Additional layer(s) made of, for example, fabric may be positioned at each side of the pressure reservoir. In some embodiments, the RF coil unit may include additional layers positioned at opposing sides of the coupling electronics and configured to cool the coupling electronics.

The coupling electronics of each RF coil element may be enclosed inside a respective plastic housing (e.g., each feed board of each RF coil element may be enclosed within a separate housing relative to each other feed board). In some embodiments, the housings of the coupling electronics may be shaped to seat within the openings of the pressure reservoir (e.g., each housing may have approximately a same shape as each opening of the pressure reservoir). For each RF coil element, MRI signals may be received (e.g., measured) by the loop portion and processed by the corresponding coupling electronics of the RF coil element. The coupling electronics may then transmit electronic signals to the MRI system via an output cable.

Turning now to FIG. 1, a magnetic resonance imaging (MRI) apparatus 10 is illustrated. MRI apparatus 10 includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, a data processing unit 31, an operating console unit 32, and a display unit 33. In some embodiments, the RF coil unit 14 is a surface coil, which is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI apparatus 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI apparatus 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI apparatus 10 and replaced with another RF coil unit, the RF body coil unit 15 is fixedly attached and connected to the MRI apparatus 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coil unit (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the data processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the data processing unit 31 and the display unit 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform predetermined data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image on the display screen of the display device based on control signals received from the controller unit 25. The display unit 33 displays, for example, an image regarding an input item about which the operator inputs operation data from the operating console unit 32. The display unit 33 also displays a two-dimensional (2D) slice image or three-dimensional (3D) image of the subject 16 generated by the data processing unit 31.

Figure 2:
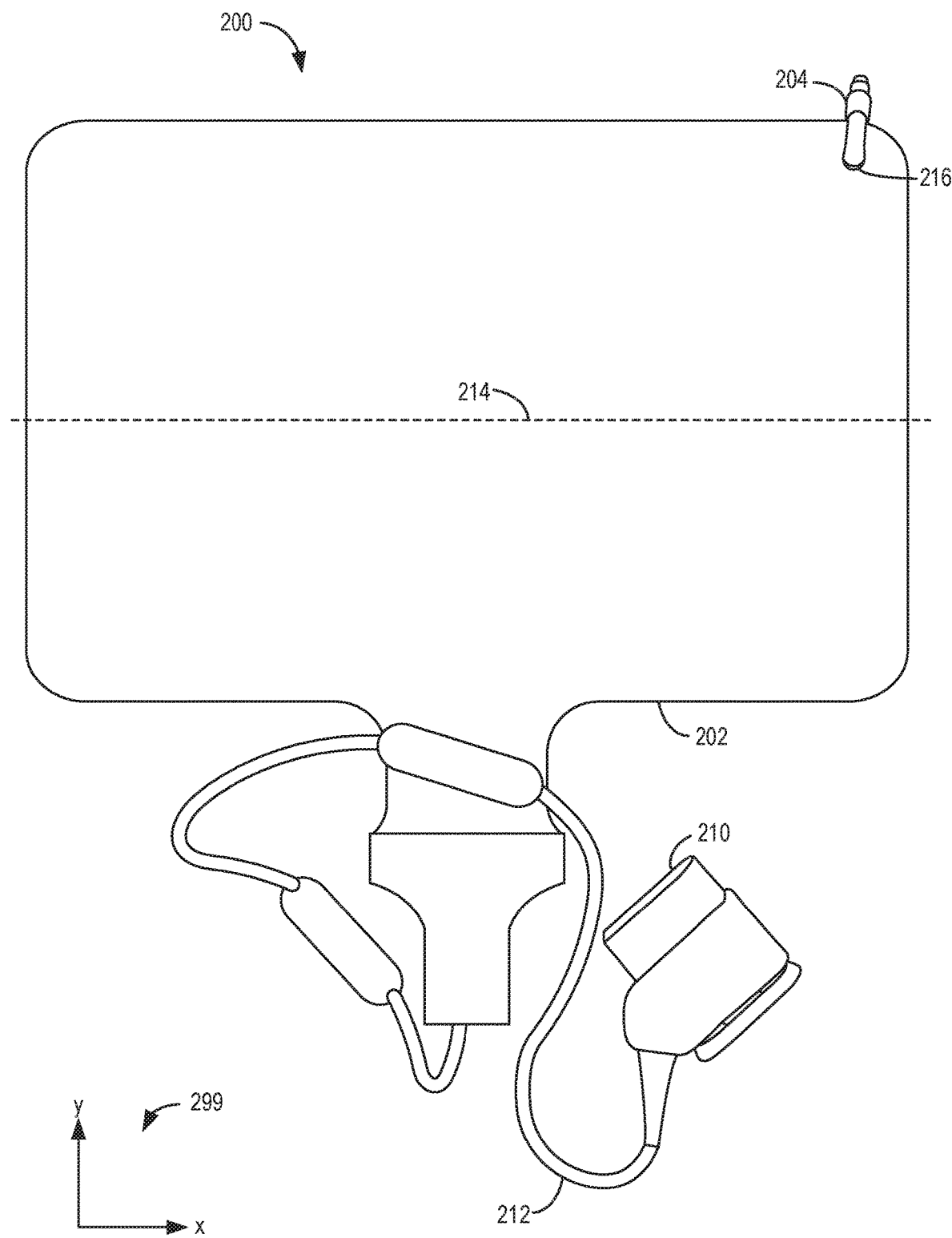
FIG. 2 shows an RF coil unit in an assembled configuration, according to an exemplary embodiment.

Now referring to FIG. 2, an RF coil unit 200 in an assembled configuration is shown, according to an exemplary embodiment. The RF coil unit 200 may be used as the RF coil unit 14 described above with reference to FIG. 1. RF coil unit 200 includes an outer layer 202 forming an exterior of the RF coil unit 200. In some embodiments, the outer layer 202 may be formed of a relatively soft and flexible material (e.g., fabric). An interior of the RF coil unit 200 includes a plurality of flexible RF coil elements and an adjustable pressure reservoir, as described further below. Each of the RF coil elements may include a loop portion electronically coupled to respective coupling electronics (e.g., feed board). The RF coil elements may receive MR signals, process, and transmit to an output connector 210 of the RF coil unit 200 via a coil-interfacing cable 212 electronically coupled to the coupling electronics of each RF coil element. The output connector 210 may interface with an input of an MRI system (e.g., controller unit 25 of MRI apparatus 10 shown by FIG. 1 and described above) in order to image a subject (e.g., a patient) via the RF coil unit 200 and MRI system.

The pressure reservoir disposed within the interior of the RF coil unit 200 includes a sealed chamber formed by, for example, plastic, leather, or any other appropriate material. The sealed chamber fluidly coupled to a fluid passage 204 extending through the outer layer 202 via an opening 216 of the outer layer 202. The fluid passage 204 may include one or more valves (e.g., check valves) configured to maintain a pressure (e.g., gas pressure) within the pressure reservoir. For example, a care provider (e.g., clinician) may couple the fluid passage 204 to a vacuum pump in order to remove gases from the interior of the pressure reservoir and decrease the pressure within the pressure reservoir relative to ambient air pressure (e.g., atmospheric pressure). In some embodiments, the fluid passage 204 may include a first valve (e.g., check valve) enabling gases to flow out of the pressure reservoir but not into the pressure reservoir. The fluid passage 204 may additionally include a second valve (e.g., pressure relief valve) configured to enable gases to flow into the pressure reservoir during conditions in which the second valve is in an opened position (e.g., to expand the pressure reservoir from a compressed condition to an uncompressed condition) and to prevent gases from flowing into the pressure reservoir during conditions in which the second valve is in a fully closed position. The first valve and/or second valve may be normally closed valves that do not enable gases to flow into and/or out of the pressure reservoir during conditions in which the valves are in a fully closed position. However, the first valve and/or second valve may be actuated (e.g., electrically actuated via the processing system of the MRI system, physically actuated by an operator of the MRI system, etc.) from the fully closed position to an opened position in order to adjust the pressure within the pressure reservoir (e.g., increase or decrease the gas pressure within the pressure reservoir).

As one example, the care provider may couple the fluid passage 204 to the vacuum pump, which may open the first valve in order to flow gases out of the pressure reservoir without flowing gases into the pressure reservoir (e.g., while maintaining the second valve in the fully closed position). As a result, the pressure of the pressure reservoir is decreased, pellets disposed within the pressure reservoir may be compressed together, and the RF coil unit 200 is formed against a body of a subject to be imaged. The first valve may then automatically close when the vacuum pump is decoupled from the fluid passage to maintain the lowered pressure of the pressure reservoir. Maintaining the pressure of the pressure reservoir in this way may maintain a shape of the RF coil unit relative to the body of the subject. When a scan is over, the care provider may actuate the second valve to an opened position to flow ambient air into the pressure reservoir. As a result, the pressure within the pressure reservoir may adjust to be approximately equal to ambient air pressure (e.g., atmospheric air pressure external to the interior of the pressure reservoir), and the pellets disposed within the interior of the pressure reservoir may no longer be compressed together. Flowing ambient air into the pressure reservoir in this way (e.g., relieving the pressure within the pressure reservoir) may restore the shape of the RF coil unit 200 to its normal, uncompressed shape (e.g., the shape shown by FIG. 2).

In some embodiments, at least one of the valves described above may be formed together with the fluid passage 204 as a single piece (e.g., integrated together with the fluid passage as a single unit). In FIG. 2, the RF coil unit 200 is substantially rectangular. It should be understood that the RF coil unit can be any appropriate shape, such as square, circle, oval, and so on, for various applications. The RF coil unit can also be any appropriate size, according to applications.

Now referring to FIG. 3, an interior portion of the RF coil unit 200 of FIG. 2 is shown. FIG. 3 shows the RF coil unit 200 in partial cross-section in order to illustrate a relative arrangement of the RF coil loop portions, coupling electronics, pressure reservoir, and other components of the RF coil unit 200. Various different views of the RF coil unit 200 are shown by FIGS. 2-5, and reference axes 299 are included for comparison of the different views.

The RF coil unit 200 includes eight (8) RF coil elements arranged to form an RF coil array. Each coil element includes a loop portion and a coupling electronics portion electrically connected to the loop portion. Specifically, RF coil unit 200 includes a first row of RF coil elements including a first loop portion 334 and first coupling electronics portion 318, a second loop portion 336 and second coupling electronics portion 320, a third loop portion 338 and third coupling electronics portion 322, and a fourth loop portion 340 and fourth coupling electronics portion 324 (e.g., with first loop portion 334 and first coupling electronics portion 318 corresponding to the first RF coil element, second loop portion 336 and second coupling electronics portion 320 corresponding to the second RF coil element, and so forth). The RF coil unit 200 additionally includes a second row of RF coil elements including a fifth loop portion 342 and fifth coupling electronics portion 326, a sixth loop portion 344 and sixth coupling electronics portion 328, a seventh loop portion 346 and seventh coupling electronics portion 330, and an eighth loop portion 348 and eighth coupling electronics portion 332. The RF coil elements of the first row may partially overlap the RF coil elements of the second row. For example, first loop portion 334 partially overlaps fifth loop portion 342, second loop portion 336 partially overlaps sixth loop portion 344, etc. Further, within each row, adjacent RF coil elements may partially overlap each other. For example, first loop portion 334 partially overlaps adjacent second loop portion 336, fifth loop portion 342 partially overlaps adjacent sixth loop portion 344, etc. Each RF coil element may be electronically isolated from each other RF coil element, such that the overlapping of the RF coil elements does not interfere with MR signals acquired by the RF coil elements to image a body of a subject. In some embodiments, the RF coil unit 200 may include a different number of RF coil elements (e.g., 12 RF coil elements, 16 RF coil elements, etc.).

In some embodiments, the loop portions may be arranged along a layer of flexible cloth material such that the loop portions are positioned between the layer of cloth material and the pressure reservoir 300. The loop portion of each RF coil element may be fixed (e.g., stitched) to the cloth material. In other embodiments, the cloth material may be positioned between the loop portions and the pressure reservoir 300, with the loop portions fixed to the cloth material.

Each RF coil element is coupled (e.g., electronically coupled) to respective coupling electronics (e.g., feed board). In some embodiments, each feed board is packaged within a respective housing. In some embodiments, the housings may be formed from a plastic material.

In some embodiments, each of the coupling electronics portion is seated within a respective opening of the pressure reservoir 300. Specifically, first coupling electronics portion 318 is seated within first opening 302, second coupling electronics portion 320 is seated within second opening 304, third coupling electronics portion 322 is seated within third opening 306, fourth coupling electronics portion 324 is seated within fourth opening 308, fifth coupling electronics portion 326 is seated within fifth opening 310, sixth coupling electronics portion 328 is seated within sixth opening 312, seventh coupling electronics portion 330 is seated within seventh opening 314, and eighth coupling electronics portion 332 is seated within eighth opening 316. Each of the openings of the pressure reservoir 300 extends through the pressure reservoir 300 (e.g., extends entirely through the pressure reservoir 300 from a first side 301 of the pressure reservoir 300, as shown by FIG. 4, to an opposing, second side 303 of the pressure reservoir 300). Each of the openings is not fluidly coupled to an interior of the pressure reservoir 300 (e.g., gases such as air maintained within the interior of the pressure reservoir 300 do not flow into or out of the interior of the pressure reservoir 300 at any of the first opening 302, second opening 304, third opening 306, fourth opening 308, fifth opening 310, sixth opening 312, seventh opening 314, or eighth opening 316). The sidewalls (e.g., inner sidewalls, such as inner sidewall 337, which are offset or spaced apart from outer sidewalls forming an outer perimeter of the pressure reservoir 300, such as outer sidewall 339) of the pressure reservoir 300 are sealed at each of the openings configured to receive the housings of the coupling electronics, such that each of the openings forms a respective through-hole between the first side 301 and second side 303 of the pressure reservoir 300. Each of the openings (which may be referred to herein as through-holes) is sealed such that the openings fluidly isolate an interior of the pressure reservoir 300 from ambient atmosphere (e.g., gas does not flow between the interior of the pressure reservoir 300 and ambient atmosphere via the openings).

The coupling electronics may be coupled to an output board 354 via respective electrical wires, as shown by FIGS. 3-4, and the output board 354 may output electrical signals from each of the coupling electronics to the coil-interfacing cable 212. The RF coil unit 200 may additionally include one or more baluns 350 and 352 electrically coupled between the output board 354 and the coupling electronics of each RF coil element. The coil-interfacing cable 212 may be coupled to an MRI system as described above in order to transmit the signals from the RF coil elements to the MM system for imaging of a subject via the RF coil unit 200.

In some embodiments, each of the openings of the pressure reservoir 300 (e.g., first opening 302, second opening 304, third opening 306, fourth opening 308, fifth opening 310, sixth opening 312, seventh opening 314, and eighth opening 316) may be covered (e.g., closed or capped) with respective thermal patches 358 and thermal patches 400, as shown by the exploded view of FIG. 4. Specifically, as described above, when the RF coil unit 200 is fully assembled, the coupling electronics are seated within the respective openings of the pressure reservoir 300. The openings may be covered at the first side 301 of the pressure reservoir 300 by thermal patches 358, and the openings may be covered at the second side 303 of the pressure reservoir by thermal patches 400, with the housings positioned between the thermal patches 358 and thermal patches 400 within the openings. In this configuration, the thermal patches 358 and thermal patches 400 may aid in retaining the coupling electronics within the corresponding openings. Further, in some embodiments, thermal patches 358 and/or thermal patches 400 may be formed from materials having high thermal conductivity. As a result, the thermal patches 358 at the first side 301 and thermal patches 400 at the second side 303 may increase a transfer of heat away from the housings when the RF coil unit 200 is utilized to image a subject (e.g., a patient). An operating temperature of the coupling electronics may be reduced by the thermal patches, resulting in increased patient comfort.

In order to further increase patient comfort, in some embodiments, the RF coil unit 200 may include a first plurality of flexible spacers 356 positioned between the first side 301 of the pressure reservoir 300 and a first outer layer 360 of the RF coil unit 200, and/or a second plurality of flexible spacers 402 positioned between the second side 303 of the pressure reservoir 300 and an opposing, second outer layer 364 of the RF coil unit 200. The first outer layer 360 and the second outer layer 364 may correspond to the outer layer 202 in FIG. 2. In some embodiments, the first and second outer layers 360 and 364 are made of one piece of material being folded. In some embodiments, the first and second outer layers 360 and 364 are made of two pieces of material that are stitched together to form the exterior of the RF coil unit 200. The flexible spacers 356 and flexible spacers 402 may be formed from a foam material in some embodiments. In other embodiments, the flexible spacers 356 and flexible spacers 402 may be formed from fire-retardant material. In some embodiments, each of the flexible spacers 356 at the first side 301 may be positioned in contact with a respective thermal patch of thermal patches 358 (e.g., positioned directly against the respective thermal patch without other components between), and each of the flexible spacers 402 at the second side 303 may be positioned in contact with a respective thermal patch of thermal patches 400. The flexible spacers 356 and flexible spacers 402 may increase an amount of air within the RF coil unit 200 surrounding the openings of the pressure reservoir 300 which may reduce a temperature of the coupling electronics during operation.

After the RF coil unit 200 is fully assembled along assembly axis 499, the coupling electronics within each housing are coupled to both of the RF coil elements at the second side 303 and the electrical wires at the first side 301. In this configuration, each RF coil element positioned at the second side 303 is electrically coupled to a corresponding electrical wire positioned at the first side 301 by coupling electronics within a corresponding housing, with each electrical wire joined to the output board 354 at the first side 301.

The relative arrangement of the RF coil elements, pressure reservoir 300, and housings is further illustrated by the cross-sectional view of the RF coil unit 200 shown by FIG. 5 (taken along axis 214 shown by FIGS. 2-3). As appreciated in FIG. 5, the pressure reservoir 300 may include loose fill that includes a plurality of particles within the pressure reservoir, such as pellets 510, in the interior volume of the pressure reservoir. The pellets may be comprised of polystyrene or other suitable material.

In some embodiments, the outer layers of the RF coil unit 200 (e.g., first outer layer 360 and second outer layer 364) may include multiple sub-layers and/or different types of material. In the embodiment shown by FIG. 5, the second outer layer 364 includes three sub-layers, with each sub-layer formed from a different material. Specifically, the second outer layer 364 includes outermost sub-layer 502, innermost sub-layer 506, and mid sub-layer 504. In some embodiments, the innermost sub-layer 506 may be formed of fire-retardant fabric material, the mid sub-layer 504 may be formed of fire-retardant material, and the outermost sub-layer 502 may be formed of polyurethane-coated fabric material. However, in other embodiments, the outer layers may include a different number of sub-layers and/or different types of materials.

Figure 6:
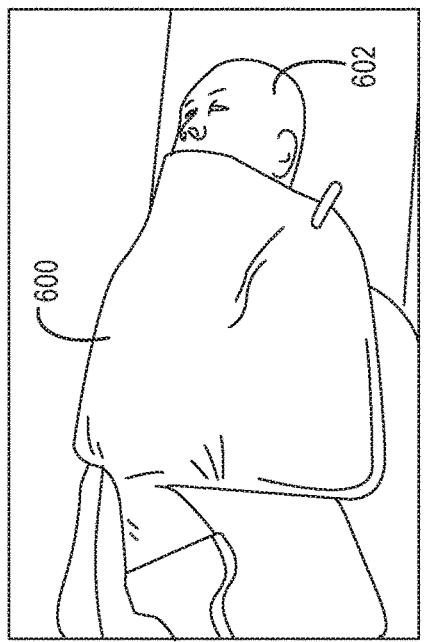
FIGS. 6-13 each show different configurations of an RF coil unit coupled to subject anatomy, according to an exemplary embodiment.
Figure 7:
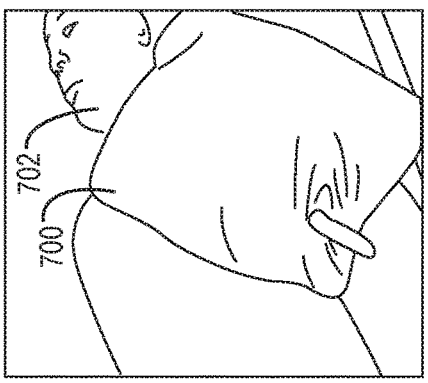
Figure 8:
Figure 9:
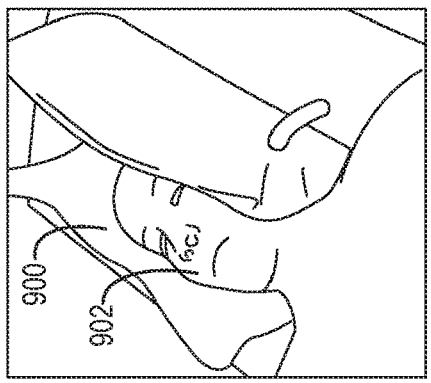
Figure 10:
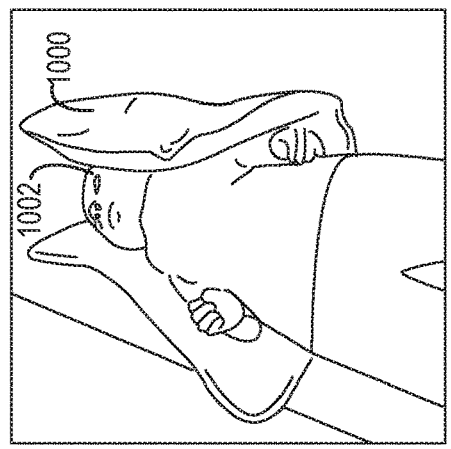
Figure 11:
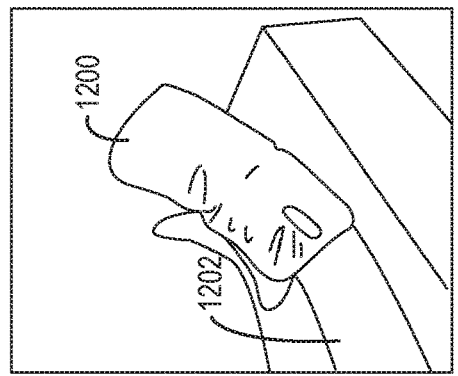
Figure 12:
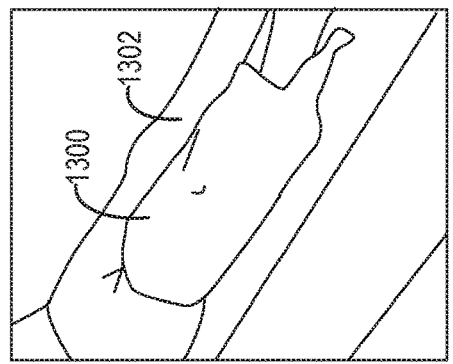
Figure 13:
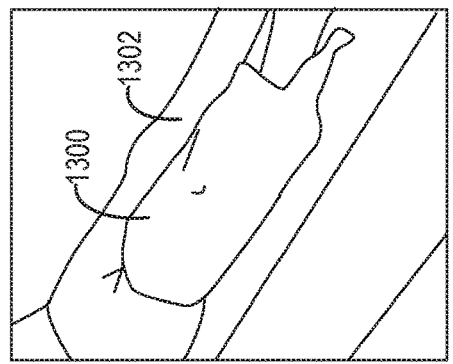
Figure 14:
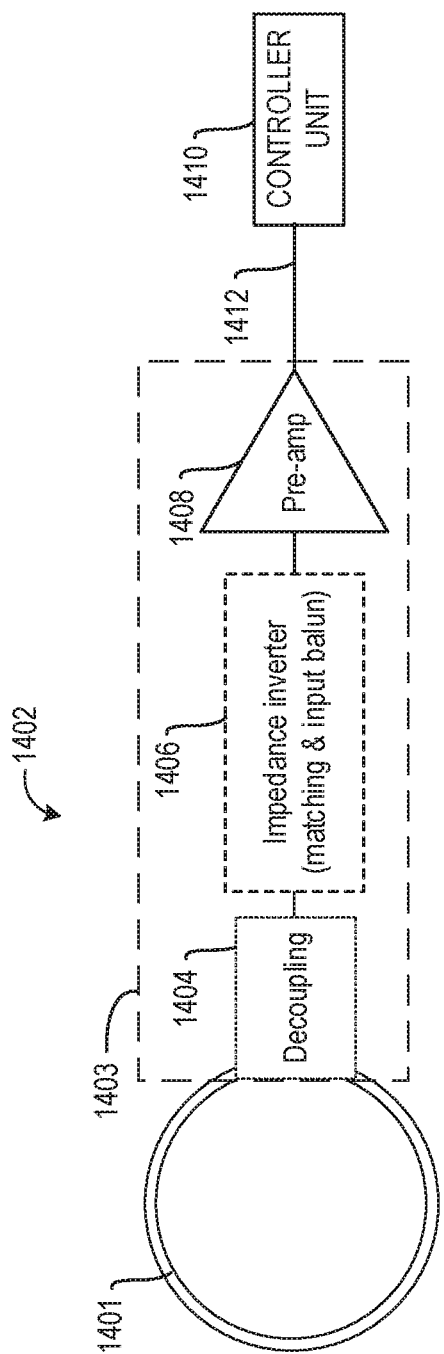
FIG. 14 schematically shows an example RF coil element of an RF coil unit coupled to a controller unit, according to an exemplary embodiment.

Referring now to FIGS. 6-13, various coupled configurations of an RF coil units are shown. Specifically, FIG. 6 shows RF coil unit 600 formed to subject 602, FIG. 7 shows RF coil 700 formed to subject 702, FIG. 8 shows RF coil 800 formed to subject 802, FIG. 9 shows RF coil 900 formed to subject 902, FIG. 10 shows RF coil 1000 formed to subject 1002, FIG. 11 shows RF coil 1100 formed to subject 1102, FIG. 12 shows RF coil 1200 formed to subject 1202, and FIG. 13 shows RF coil 1300 formed to subject 1302. Each of the RF coil units 600, 700, 800, 900, 1000, 1100, 1200, and 1300 may be the same as the RF coil unit 200 described above with reference to FIGS. 2-5, in some embodiments. Each of the RF coil units includes a pressure reservoir, which may be the same as the pressure reservoir 300 described above. In each of FIGS. 6-13, the pressure (e.g., gas pressure) within the interior of the pressure reservoir is reduced below atmospheric pressure in order to form the RF coil unit to the body of the subject, similar to the examples described above (e.g., such that pellets disposed within the interior of the pressure reservoir are compressed to increase a rigidity of the pressure reservoir and RF coil unit).

FIG. 6 shows RF coil unit 600 formed to the neck and chest of subject 602, FIG. 7 shows RF coil unit 700 formed to a shoulder of subject 702, FIG. 8 shows RF coil unit 800 formed to the head and neck of subject 802, FIG. 9 shows RF coil unit 900 formed to the head of subject 902, FIG. 10 shows RF coil unit 1002 formed to the torso of subject 1002 (e.g., an infant), FIG. 11 shows RF coil unit 1100 formed to the lower back of subject 1102, FIG. 12 shows RF coil unit 1200 formed to a foot of subject 1202, and FIG. 13 shows RF coil unit 1300 formed to a knee of subject 1302. As described above, in some embodiments, each of the RF coil units shown by FIGS. 6-13 may be the same as the RF coil unit 200 shown by FIGS. 2-5 and described above. The RF coil unit 200 may thus be formed to the multiple different anatomical structures of a subject to be imaged shown by FIGS. 6-13. The examples shown by FIGS. 6-13 are not limiting and in some embodiments, the RF coil unit 200 may be formed to other anatomical features of a subject (e.g., a thigh, arm, upper back, etc. of the subject).

Turning now to FIG. 14, a schematic view of an RF coil element 1402 including a loop portion 1401 coupled to a controller unit 1410 via coupling electronics portion 1403 and a coil-interfacing cable 1412 is shown. The RF coil element 1402 is one non-limiting example of an RF coil element of RF coil unit 200.

In some embodiments, the loop portion 1401 may be a distributed capacitance loop portion (also known as "Air Coil"), as disclosed in Patent Application PCT/US2017/062971, which is incorporated herein by reference for all purposes. In other embodiments, the loop portion 1401 may be any appropriate flexible coil (e.g., a coil including copper wires and discrete capacitors).

The coupling electronics portion 1403 may be coupled to the loop portion of the RF coil element 1402. In some embodiments, the coupling electronics portion 1403 may include a decoupling circuit 1404, impedance inverter circuit 1406, and a pre-amplifier 1408. The decoupling circuit 1404 may effectively decouple the RF coil element 1402 during a transmit operation. Typically, the RF coil element 1402 in its receive mode may be coupled to a body of a subject being imaged by the MR apparatus in order to receive electromagnetic radiation from the body. The RF coil element 1402 may be decoupled from the RF body coil while the RF body coil is transmitting the RF signal. The decoupling of the receive coil from the transmit coil may be achieved using resonance circuits and PIN diodes, microelectromechanical systems (MEMS) switches, or another type of switching circuitry. Herein, the switching circuitry may activate detuning circuits operatively connected to the RF coil element 1402.

The impedance inverter circuit 1406 may form an impedance matching network between the RF coil element 1402 and the pre-amplifier 1408. The impedance inverter circuit 1406 is configured to transform a coil impedance of the RF coil element 1402 into an optimal source impedance for the pre-amplifier 1408. The impedance inverter circuit 1406 may include an impedance matching network and an input balun. The pre-amplifier 1408 receives MR signals from the corresponding RF coil element 1402 and amplifies the received MR signals. In one example, the pre-amplifier may have a low input impedance that is configured to generate a relatively high impedance in the coil to reduce the coupling between coil elements in receive mode.

The coil-interfacing cable 1412, such as an RF coil array interfacing cable, may be used to transmit signals between the RF coil elements of the RF coil unit and other aspects of the processing system, for example to control the RF coil elements and/or to receive information from the RF coil elements.

The technical effect of configuring the RF coil unit to form to the body of the patient by adjusting the gas pressure within the pressure reservoir is to position the RF coil elements closer to the body of the patient to increase SNR, with the coupling electronics of the RF coil elements positioned within the openings of the pressure reservoir to increase thermal performance of the RF coil unit and increase patient comfort.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A radio frequency (RF) coil unit for magnetic resonance imaging (MRI) comprising:
   an outer layer forming exterior of the RF coil unit;
   a pressure reservoir enclosed by the outer layer, wherein the pressure reservoir forms a sealed chamber and wherein the pressure reservoir includes a plurality of openings extending through the pressure reservoir, wherein each of the plurality of openings is fluidly isolated from a pressurizing fluid inside the pressure reservoir; and an array of RF coil elements enclosed by the outer layer, wherein the array of RF coil elements is disposed outside of the sealed chamber of the pressure reservoir, wherein each RF coil element includes a coupling electronics portion seated within one of the plurality of openings.

2. The RF coil unit of claim 1, further comprising a layer of cloth material disposed between the pressure reservoir and loop portions, wherein the loop portions are fixed to the layer of cloth material.

3. The RF coil unit of claim 1, further comprising a layer of cloth material to which loop portions are fixed, wherein the loop portions are disposed between the pressure reservoir and the layer of the cloth material.

4. The RF coil unit of claim 1, wherein the pressure reservoir further comprises a plurality of particles within the sealed chamber.

5. The RF coil unit of claim 1, further comprising a plurality of spacers disposed between the outer layer and the pressure reservoir.

6. The RF coil unit of claim 1, further comprising loose pellets disposed within an interior volume of the pressure reservoir, wherein reducing a pressure of the pressure reservoir compresses the loose pellets and increases a rigidity of the pressure reservoir.

7. The RF coil unit of claim 1, further comprising a fluid passage which fluidly couples the sealed chamber to ambient atmosphere.

8. The RF coil unit of claim 7, wherein a pressure inside the pressure reservoir is reduced by flowing a gas out of the pressure reservoir to the ambient atmosphere, the pressure is increased by flowing the gas into the pressure reservoir from the ambient atmosphere.

9. The RF coil unit of claim 1, further comprising a coil-interfacing cable which electrically couples the array of RF coil elements to an MRI system.

10. The RF coil unit of claim 9, further comprising an output board which electrically couples the array of RF coil elements to the coil-interfacing cable.

11. A radio frequency (RF) coil unit for magnetic resonance imaging (MRI) comprising:
an outer layer forming an exterior of the RF coil unit;
a pressure reservoir enclosed by the outer layer, wherein the pressure reservoir forms a sealed chamber, and wherein the pressure reservoir includes a plurality of openings extending through the pressure reservoir;
an array of RF coil elements and an array of coupling electronics portions enclosed by the outer layer, wherein each RF coil element comprises,
a loop portion disposed on one side of the pressure reservoir, and
one of the array of coupling electronics portions, wherein each of the plurality of openings includes one of the array of coupling electronics portions seated within a corresponding opening.

12. The RF coil unit of claim 11, wherein each RF coil element further comprises an electrical wire electrically coupled to the coupling electronics portion, wherein the electrical wire and the loop portion are disposed on opposing sides of the pressure reservoir.

13. The RF coil unit of claim 11, further comprising a plurality of thermal patches disposed on both sides of the coupling electronics portions.

14. A radio frequency (RF) coil unit for magnetic resonance imaging (MRI), comprising:
an outer layer forming an exterior of the RF coil unit;
an opening extending through the outer layer to an interior of the RF coil unit;
a pressure reservoir enclosed by the outer layer within the interior, the pressure reservoir including a plurality of through-holes formed by inner sidewalls of the pressure reservoir, the inner sidewalls offset from outer sidewalls of the pressure reservoir, wherein each of the plurality of through-holes extends entirely through the pressure reservoir from a first side of the pressure reservoir to a second side of the pressure reservoir, the first side of the pressure reservoir opposite the second side of the pressure reservoir;
a fluid passage extending to the exterior of the RF coil unit though the opening of the outer layer, the fluid passage fluidly coupled to the pressure reservoir; and
an array of RF coil elements enclosed by the outer layer, wherein each RF coil element comprises,
a loop portion disposed on one side of the pressure reservoir, and
a coupling electronics portion seated within a corresponding through-hole of the plurality of through-holes of the pressure reservoir.

15. The RF coil unit of claim 14, further comprising a plurality of thermal patches positioned at opposing sides of the pressure reservoir, where each through-hole of the plurality of through-holes is closed by a corresponding thermal patch of the plurality of thermal patches.

16. The RF coil unit of claim 14, wherein the fluid passage is configured to couple to a vacuum source to flow gas from the pressure reservoir to ambient atmosphere.

17. The RF coil unit of claim 14, wherein the fluid passage includes a valve configured to fluidly isolate the pressure reservoir from ambient atmosphere in a closed position, and to fluidly couple the pressure reservoir to ambient atmosphere or a vacuum source in an opened position.

18. The RF coil unit of claim 14, wherein the pressure reservoir is sealed and fluidly isolated from ambient atmosphere at each through-hole of the plurality of through-holes by the inner sidewalls.

19. The RF coil unit of claim 14, further comprising a first plurality of thermal patches fixed to the first side of the pressure reservoir and a second plurality of thermal patches fixed to the second side of the pressure reservoir, where each coupling electronics portion is coupled to exactly one respective thermal patch of the first plurality of thermal patches and exactly one respective thermal patch of the second plurality of thermal patches.

20. The RF coil unit of claim 19, further comprising a first plurality of flexible spacers and a second plurality of flexible spacers disposed between the pressure reservoir and the outer layer, where each flexible spacer of the first plurality of flexible spacers is positioned in contact with one respective thermal patch of the first plurality of thermal patches, and where each flexible spacer of the second plurality of flexible spacers is positioned in contact with one respective thermal patch of the second plurality of thermal patches.

* * * * *